United States Patent
Moberg (10) Patent No.: US 10,434,281 B2
(45) Date of Patent: Oct. 8, 2019

(54) CLEANING DEVICE FOR MEDICAL INSTRUMENT AND METHOD OF USE

(71) Applicant: Covidien LP, Mansfield, MA (US)

(72) Inventor: John Robert Moberg, Elk River, MN (US)

(73) Assignee: Covidien LP, Mansfield, MA (US)

(*) Notice: Subject to any disclaimer, the term of this patent is extended or adjusted under 35 U.S.C. 154(b) by 191 days.

(21) Appl. No.: 15/404,323

(22) Filed: Jan. 12, 2017

(65) Prior Publication Data
US 2017/0119996 A1    May 4, 2017

Related U.S. Application Data

(63) Continuation of application No. 14/026,009, filed on Sep. 13, 2013, now Pat. No. 9,579,157.
(Continued)

(51) Int. Cl.
*A61B 90/70* (2016.01)
*A61L 2/00* (2006.01)
(Continued)

(52) U.S. Cl.
CPC .............. *A61M 25/00* (2013.01); *A61B 90/70* (2016.02); *B08B 3/14* (2013.01); *B08B 9/023* (2013.01);
(Continued)

(58) Field of Classification Search
CPC ........... A61M 2025/0019; A61B 19/34; A61B 2019/343; A61B 1/00142; A61B 1/121;
(Continued)

(56) References Cited

U.S. PATENT DOCUMENTS

| 1,481,078 A | 1/1924 | Albertson |
| 2,178,790 A | 11/1939 | Henry |

(Continued)

FOREIGN PATENT DOCUMENTS

| CA | 2000621 | 10/1989 |
| CN | 101795630 A | 8/2010 |

(Continued)

OTHER PUBLICATIONS

Amplatz Coronary Catheters, posted: Feb. 25, 2009, [online], [retrieved on Mar. 29, 2011], retrieved from the Cardiophile MD using Internet website <URL:http://cardiophile.org/2009/02/amplatzcoronary-catheter.html> (3 pages).
(Continued)

*Primary Examiner* — Joseph L. Perrin
*Assistant Examiner* — Irina Graf (57) ABSTRACT

A cleaning device includes a flushing chamber having opposite proximal and distal ends, and a length extending between the proximal and distal ends. An inlet port of the cleaning device is in fluid communication with the flushing chamber and configured for fluid connection to a source of fluid. The flushing chamber is selectively openable along its length to an open position, in which the distal end portion of the medical instrument is insertable into the flushing chamber, and selectively closable along its length to a closed position, in which the distal end portion of the medical instrument is enclosed and fluidly sealed within the flushing chamber.

16 Claims, 8 Drawing Sheets

Related U.S. Application Data (60) Provisional application No. 61/700,636, filed on Sep. 13, 2012.

(51) Int. Cl.
*B08B 9/32* (2006.01)
*A61M 25/00* (2006.01)
*B08B 3/14* (2006.01)
*B08B 9/023* (2006.01)
*B08B 9/032* (2006.01)
*A61B 17/3207* (2006.01)

(52) U.S. Cl.
CPC .......... *B08B 9/0321* (2013.01); *B08B 9/0328* (2013.01); *A61B 17/320783* (2013.01); *A61B 2090/701* (2016.02); *A61M 2025/0019* (2013.01); *B08B 2209/032* (2013.01)

(58) Field of Classification Search
CPC ......... A61B 1/125; A61B 1/126; A61B 90/70; A61B 90/701; B08B 1/00; B08B 3/04; B08B 9/02; A61L 2/18; A61L 2202/24
See application file for complete search history.

(56) References Cited

U.S. PATENT DOCUMENTS

| | | |
|---|---|---|
| 2,701,559 A | 2/1955 | Cooper |
| 2,850,007 A | 9/1958 | Lingley |
| 3,064,651 A | 11/1962 | Henderson |
| 3,082,805 A | 3/1963 | Royce |
| 3,320,957 A | 5/1967 | Sokolik |
| 3,614,953 A | 10/1971 | Moss |
| 3,683,891 A | 8/1972 | Eskridge et al. |
| 3,705,577 A | 12/1972 | Sierra |
| 3,732,858 A | 5/1973 | Banko |
| 3,749,085 A | 7/1973 | Willson et al. |
| 3,800,783 A | 4/1974 | Jamshidi |
| 3,815,604 A | 6/1974 | O'Malley et al. |
| 3,831,585 A | 8/1974 | Brondy et al. |
| 3,837,345 A | 9/1974 | Matar |
| 3,845,375 A | 10/1974 | Stiebel |
| 3,937,222 A | 2/1976 | Banko |
| 3,945,375 A | 3/1976 | Banko |
| 3,976,077 A | 8/1976 | Kerfoot, Jr. |
| 3,995,619 A | 12/1976 | Glatzer |
| 4,007,732 A | 2/1977 | Kvavle et al. |
| 4,020,847 A | 5/1977 | Clark, III |
| 4,030,503 A | 6/1977 | Clark, III |
| 4,034,744 A | 7/1977 | Goldberg |
| 4,038,985 A | 8/1977 | Chiulli |
| 4,112,708 A | 9/1978 | Fukuda |
| 4,177,797 A | 12/1979 | Baylis et al. |
| 4,210,146 A | 7/1980 | Banko |
| 4,273,128 A | 6/1981 | Lary |
| 4,306,562 A | 12/1981 | Osborne |
| 4,306,570 A | 12/1981 | Matthews |
| 4,349,032 A | 9/1982 | Koyata |
| 4,368,730 A | 1/1983 | Sharrock |
| 4,424,045 A | 1/1984 | Kulischenko et al. |
| 4,436,091 A | 3/1984 | Banko |
| 4,445,509 A | 5/1984 | Auth |
| 4,490,139 A | 12/1984 | Huizenga et al. |
| 4,494,057 A | 1/1985 | Hotta |
| 4,512,344 A | 4/1985 | Barber |
| 4,589,412 A | 5/1986 | Kensey |
| 4,603,694 A | 8/1986 | Wheeler |
| 4,620,547 A | 11/1986 | Boebel |
| 4,631,052 A | 12/1986 | Kensey |
| 4,646,719 A | 3/1987 | Neuman et al. |
| 4,646,736 A | 3/1987 | Auth |
| 4,646,738 A | 3/1987 | Trott |
| 4,649,919 A | 3/1987 | Thimsen et al. |
| 4,653,496 A | 3/1987 | Bundy |
| 4,664,112 A | 5/1987 | Kensey et al. |
| 4,669,469 A | 6/1987 | Gifford, III et al. |
| 4,679,558 A | 7/1987 | Kensey et al. |
| 4,686,982 A | 8/1987 | Nash |
| 4,692,141 A | 9/1987 | Mahurkar |
| 4,696,298 A | 9/1987 | Higgins et al. |
| 4,696,667 A | 9/1987 | Masch |
| 4,705,038 A | 11/1987 | Sjostrom et al. |
| 4,706,671 A | 11/1987 | Weinrib |
| 4,728,319 A | 3/1988 | Masch |
| 4,729,763 A | 3/1988 | Henrie |
| 4,730,616 A | 3/1988 | Frisbie et al. |
| 4,732,154 A | 3/1988 | Shiber |
| 4,733,662 A | 3/1988 | DeSatnick et al. |
| 4,745,919 A | 5/1988 | Bundy et al. |
| 4,747,406 A | 5/1988 | Nash |
| 4,747,821 A | 5/1988 | Kensey et al. |
| 4,749,376 A | 6/1988 | Kensey et al. |
| 4,754,755 A | 7/1988 | Husted |
| 4,757,819 A | 7/1988 | Yokoi et al. |
| 4,765,332 A | 8/1988 | Fischell et al. |
| 4,771,774 A | 9/1988 | Simpson et al. |
| 4,781,186 A | 11/1988 | Simpson et al. |
| 4,784,636 A | 11/1988 | Rydell |
| 4,790,812 A | 12/1988 | Hawkins, Jr. et al. |
| 4,794,931 A | 1/1989 | Yock |
| 4,817,613 A | 4/1989 | Jaraczewski et al. |
| 4,819,634 A | 4/1989 | Shiber |
| 4,819,635 A | 4/1989 | Shapiro |
| 4,838,268 A | 6/1989 | Keith et al. |
| 4,842,579 A | 6/1989 | Shiber |
| 4,844,064 A | 7/1989 | Thimsen et al. |
| 4,848,343 A | 7/1989 | Wallsten et al. |
| 4,850,957 A | 7/1989 | Summers |
| 4,857,046 A | 8/1989 | Stevens et al. |
| 4,867,157 A | 9/1989 | McGurk-Burleson et al. |
| 4,870,953 A | 10/1989 | DonMicheal et al. |
| 4,883,458 A | 11/1989 | Shiber |
| 4,886,061 A | 12/1989 | Fischell et al. |
| 4,886,490 A | 12/1989 | Shiber |
| 4,887,613 A | 12/1989 | Farr et al. |
| 4,889,061 A | 12/1989 | McPherson et al. |
| 4,894,051 A | 1/1990 | Shiber |
| 4,899,757 A | 2/1990 | Pope, Jr. et al. |
| 4,919,133 A | 4/1990 | Chiang |
| 4,923,462 A | 5/1990 | Stevens |
| 4,926,858 A | 5/1990 | Gifford, III et al. |
| 4,928,693 A | 5/1990 | Goodin et al. |
| 4,936,987 A | 6/1990 | Persinski et al. |
| RE33,258 E | 7/1990 | Onik et al. |
| 4,950,238 A | 8/1990 | Sullivan |
| 4,954,338 A | 9/1990 | Mattox |
| 4,957,482 A | 9/1990 | Shiber |
| 4,966,604 A | 10/1990 | Reiss |
| 4,973,409 A | 11/1990 | Cook |
| 4,979,939 A | 12/1990 | Shiber |
| 4,979,951 A | 12/1990 | Simpson |
| 4,986,807 A | 1/1991 | Farr |
| 4,990,134 A | 2/1991 | Auth |
| 4,994,067 A | 2/1991 | Summers |
| 4,997,435 A | 3/1991 | Demeter |
| 5,000,185 A | 3/1991 | Yock |
| 5,002,553 A | 3/1991 | Shiber |
| 5,003,918 A | 4/1991 | Olson et al. |
| 5,007,896 A | 4/1991 | Shiber |
| 5,009,659 A | 4/1991 | Hamlin et al. |
| 5,019,088 A | 5/1991 | Farr |
| 5,024,234 A | 6/1991 | Leary et al. |
| 5,024,651 A | 6/1991 | Shiber |
| 5,026,384 A | 6/1991 | Farr et al. |
| 5,029,588 A | 7/1991 | Yock et al. |
| 5,030,201 A | 7/1991 | Palestrant |
| 5,047,040 A | 9/1991 | Simpson et al. |
| 5,049,124 A | 9/1991 | Bales, Jr. |
| 5,053,044 A | 10/1991 | Mueller et al. |
| 5,054,492 A | 10/1991 | Scribner et al. |
| 5,064,435 A | 11/1991 | Porter |
| 5,071,425 A | 12/1991 | Gifford, III et al. |
| 5,074,841 A | 12/1991 | Ademovic et al. |
| 5,077,506 A | 12/1991 | Krause |

(56) References Cited

U.S. PATENT DOCUMENTS

| | | |
|---|---|---|
| 5,078,722 A | 1/1992 | Stevens |
| 5,084,010 A | 1/1992 | Plaia et al. |
| 5,085,662 A | 2/1992 | Willard |
| 5,087,265 A | 2/1992 | Summers |
| 5,092,839 A | 3/1992 | Kipperman |
| 5,092,873 A | 3/1992 | Simpson et al. |
| 5,093,079 A | 3/1992 | Bakaitis et al. |
| 5,095,911 A | 3/1992 | Pomeranz |
| 5,100,423 A | 3/1992 | Fearnot |
| 5,100,424 A | 3/1992 | Jang et al. |
| 5,100,426 A | 3/1992 | Nixon |
| 5,110,822 A | 5/1992 | Sherba et al. |
| 5,112,345 A | 5/1992 | Farr |
| 5,114,399 A | 5/1992 | Kovalcheck |
| 5,115,814 A | 5/1992 | Griffith et al. |
| 5,120,323 A | 6/1992 | Shockey et al. |
| 5,127,902 A | 7/1992 | Fischell |
| 5,127,917 A | 7/1992 | Niederhauser et al. |
| 5,135,531 A | 8/1992 | Shiber |
| 5,154,705 A | 10/1992 | Fleischhacker et al. |
| 5,154,724 A | 10/1992 | Andrews |
| 5,165,421 A | 11/1992 | Fleischhacker et al. |
| 5,176,693 A | 1/1993 | Pannek, Jr. |
| 5,178,625 A | 1/1993 | Groshong |
| 5,181,920 A | 1/1993 | Mueller et al. |
| 5,183,432 A | 2/1993 | Noguchi |
| 5,190,528 A | 3/1993 | Fonger et al. |
| 5,192,291 A | 3/1993 | Pannek, Jr. |
| 5,195,956 A | 3/1993 | Stockmeier |
| 5,211,651 A | 5/1993 | Reger et al. |
| 5,217,474 A | 6/1993 | Zacca et al. |
| 5,222,966 A | 6/1993 | Perkins et al. |
| 5,224,488 A | 7/1993 | Neuffer |
| 5,224,945 A | 7/1993 | Pannek, Jr. |
| 5,224,949 A | 7/1993 | Gomringer et al. |
| 5,226,909 A | 7/1993 | Evans et al. |
| 5,226,910 A | 7/1993 | Kajiyama et al. |
| 5,234,451 A | 8/1993 | Osypka |
| 5,242,460 A | 9/1993 | Klein et al. |
| 5,242,461 A | 9/1993 | Kortenbach et al. |
| 5,250,059 A | 10/1993 | Andreas et al. |
| 5,250,065 A | 10/1993 | Clement et al. |
| 5,263,928 A | 11/1993 | Trauthen et al. |
| 5,263,959 A | 11/1993 | Fischell |
| 5,267,955 A | 12/1993 | Hanson |
| 5,267,982 A | 12/1993 | Sylvanowicz |
| 5,269,793 A | 12/1993 | Simpson |
| 5,273,526 A | 12/1993 | Dance et al. |
| 5,282,484 A | 2/1994 | Reger |
| 5,284,486 A | 2/1994 | Kotula et al. |
| 5,285,795 A | 2/1994 | Ryan et al. |
| 5,295,493 A | 3/1994 | Radisch, Jr. |
| 5,300,085 A | 4/1994 | Yock |
| 5,306,294 A | 4/1994 | Winston et al. |
| 5,308,354 A | 5/1994 | Zacca et al. |
| 5,312,425 A | 5/1994 | Evans et al. |
| 5,312,427 A | 5/1994 | Shturman |
| 5,314,438 A | 5/1994 | Shturman |
| 5,318,032 A | 6/1994 | Lonsbury et al. |
| 5,318,528 A | 6/1994 | Heaven et al. |
| 5,318,576 A | 6/1994 | Plassche, Jr. et al. |
| 5,321,501 A | 6/1994 | Swanson et al. |
| 5,322,508 A | 6/1994 | Viera |
| 5,350,390 A | 9/1994 | Sher |
| 5,356,418 A | 10/1994 | Shturman |
| 5,358,472 A | 10/1994 | Vance et al. |
| 5,358,485 A | 10/1994 | Vance et al. |
| 5,360,432 A | 11/1994 | Shturman |
| 5,366,463 A | 11/1994 | Ryan |
| 5,368,035 A | 11/1994 | Hamm |
| 5,370,609 A | 12/1994 | Drasler et al. |
| 5,370,651 A | 12/1994 | Summers |
| 5,372,601 A | 12/1994 | Lary |
| 5,372,602 A | 12/1994 | Burke |
| 5,373,619 A | 12/1994 | Fleischhacker et al. |
| 5,373,849 A | 12/1994 | Maroney et al. |
| 5,377,682 A | 1/1995 | Ueno et al. |
| 5,378,234 A | 1/1995 | Hammerslag et al. |
| 5,383,460 A | 1/1995 | Jang et al. |
| 5,395,311 A | 3/1995 | Andrews |
| 5,395,313 A | 3/1995 | Naves |
| 5,395,335 A | 3/1995 | Jang |
| 5,397,345 A | 3/1995 | Lazarus |
| 5,402,790 A | 4/1995 | Jang et al. |
| 5,403,334 A | 4/1995 | Evans et al. |
| 5,409,454 A | 4/1995 | Fischell et al. |
| 5,413,107 A | 5/1995 | Oakley et al. |
| 5,419,774 A | 5/1995 | Willard et al. |
| 5,423,740 A | 6/1995 | Sullivan et al. |
| 5,423,799 A | 6/1995 | Shiu |
| 5,423,838 A | 6/1995 | Willard |
| 5,423,846 A | 6/1995 | Fischell |
| 5,427,107 A | 6/1995 | Milo et al. |
| 5,429,136 A | 7/1995 | Milo et al. |
| 5,431,673 A | 7/1995 | Summers et al. |
| 5,441,510 A | 8/1995 | Simpson et al. |
| 5,443,446 A | 8/1995 | Shturman |
| 5,443,497 A | 8/1995 | Venbrux |
| 5,444,078 A | 8/1995 | Yu et al. |
| 5,445,155 A | 8/1995 | Sieben |
| 5,449,369 A | 9/1995 | Imran |
| 5,451,233 A | 9/1995 | Yock |
| 5,454,809 A | 10/1995 | Janssen |
| 5,456,667 A | 10/1995 | Ham et al. |
| 5,456,689 A | 10/1995 | Kresch et al. |
| 5,458,585 A | 10/1995 | Salmon et al. |
| 5,459,570 A | 10/1995 | Swanson et al. |
| 5,464,016 A | 11/1995 | Nicholas et al. |
| 5,470,415 A | 11/1995 | Perkins et al. |
| 5,485,042 A | 1/1996 | Burke |
| 5,485,840 A | 1/1996 | Bauman |
| 5,487,729 A | 1/1996 | Avellanet et al. |
| 5,489,295 A | 2/1996 | Piplani et al. |
| 5,491,524 A | 2/1996 | Hellmuth et al. |
| 5,496,267 A | 3/1996 | Drasler et al. |
| 5,501,694 A | 3/1996 | Ressemann et al. |
| 5,503,155 A | 4/1996 | Salmon et al. |
| 5,505,210 A | 4/1996 | Clement |
| 5,507,292 A | 4/1996 | Jang et al. |
| 5,507,760 A | 4/1996 | Wynne et al. |
| 5,507,761 A | 4/1996 | Duer |
| 5,507,795 A | 4/1996 | Chiang et al. |
| 5,511,568 A | 4/1996 | Bowman et al. |
| 5,512,044 A | 4/1996 | Duer |
| 5,514,115 A | 5/1996 | Frantzen et al. |
| 5,520,189 A | 5/1996 | Malinowski et al. |
| 5,522,825 A | 6/1996 | Kropf et al. |
| 5,522,880 A | 6/1996 | Barone et al. |
| 5,527,292 A | 6/1996 | Adams et al. |
| 5,527,298 A | 6/1996 | Vance et al. |
| 5,527,325 A | 6/1996 | Conley et al. |
| 5,531,685 A | 7/1996 | Hemmer et al. |
| 5,531,690 A | 7/1996 | Solar |
| 5,531,700 A | 7/1996 | Moore et al. |
| 5,540,707 A | 7/1996 | Ressemann et al. |
| 5,549,601 A | 8/1996 | McIntyre et al. |
| 5,554,163 A | 9/1996 | Shturman |
| 5,556,408 A | 9/1996 | Farhat |
| 5,558,093 A | 9/1996 | Pomeranz |
| 5,562,726 A | 10/1996 | Chuter |
| 5,562,728 A | 10/1996 | Lazarus et al. |
| 5,569,275 A | 10/1996 | Kotula et al. |
| 5,569,276 A | 10/1996 | Jang et al. |
| 5,569,277 A | 10/1996 | Evans et al. |
| 5,569,279 A | 10/1996 | Rainin |
| 5,570,693 A | 11/1996 | Jang et al. |
| 5,571,122 A | 11/1996 | Kelly et al. |
| 5,571,130 A | 11/1996 | Simpson et al. |
| 5,575,817 A | 11/1996 | Martin |
| 5,584,842 A | 12/1996 | Fogarty et al. |
| 5,584,843 A | 12/1996 | Wulfman et al. |
| 5,609,605 A | 3/1997 | Marshall et al. |
| 5,618,293 A | 4/1997 | Sample et al. |
| 5,620,447 A | 4/1997 | Smith et al. |

(56) References Cited

U.S. PATENT DOCUMENTS

| | | |
|---|---|---|
| 5,624,457 A | 4/1997 | Farley et al. |
| 5,626,562 A | 5/1997 | Castro |
| 5,626,576 A | 5/1997 | Janssen |
| 5,628,761 A | 5/1997 | Rizik |
| 5,632,754 A | 5/1997 | Farley et al. |
| 5,632,755 A | 5/1997 | Nordgren et al. |
| 5,634,464 A | 6/1997 | Jang et al. |
| 5,643,296 A | 7/1997 | Hundertmark et al. |
| 5,643,298 A | 7/1997 | Nordgren et al. |
| 5,649,941 A | 7/1997 | Lary |
| 5,660,180 A | 8/1997 | Malinowski et al. |
| 5,662,671 A | 9/1997 | Barbut et al. |
| 5,665,098 A | 9/1997 | Kelly et al. |
| 5,669,920 A | 9/1997 | Conley et al. |
| 5,674,232 A | 10/1997 | Halliburton |
| 5,676,696 A | 10/1997 | Marcade |
| 5,676,697 A | 10/1997 | McDonald |
| 5,681,336 A | 10/1997 | Clement et al. |
| 5,682,897 A | 11/1997 | Pomeranz |
| 5,683,449 A | 11/1997 | Marcade |
| 5,683,453 A | 11/1997 | Palmaz |
| 5,688,234 A | 11/1997 | Frisbie |
| 5,695,506 A | 12/1997 | Pike et al. |
| 5,695,507 A | 12/1997 | Auth et al. |
| 5,697,944 A | 12/1997 | Lary |
| 5,700,240 A | 12/1997 | Barwick, Jr. et al. |
| 5,700,687 A | 12/1997 | Finn |
| 5,707,350 A | 1/1998 | Krause et al. |
| 5,707,376 A | 1/1998 | Kavteladze et al. |
| 5,707,383 A | 1/1998 | Bays et al. |
| 5,709,698 A | 1/1998 | Adams et al. |
| 5,713,913 A | 2/1998 | Lary et al. |
| 5,715,825 A | 2/1998 | Crowley |
| 5,716,410 A | 2/1998 | Wang et al. |
| 5,720,735 A | 2/1998 | Dorros |
| 5,724,977 A | 3/1998 | Yock et al. |
| 5,728,123 A | 3/1998 | Lemelson et al. |
| 5,733,296 A | 3/1998 | Rogers et al. |
| 5,735,816 A | 4/1998 | Lieber et al. |
| 5,741,270 A | 4/1998 | Hansen et al. |
| 5,766,192 A | 6/1998 | Zacca |
| 5,772,674 A | 6/1998 | Nakhjavan |
| 5,775,327 A | 7/1998 | Randolph et al. |
| 5,776,114 A | 7/1998 | Frantzen et al. |
| 5,776,153 A | 7/1998 | Rees |
| 5,779,643 A | 7/1998 | Lum et al. |
| 5,779,673 A | 7/1998 | Roth et al. |
| 5,779,721 A | 7/1998 | Nash |
| 5,779,722 A | 7/1998 | Shturman et al. |
| 5,792,157 A | 8/1998 | Mische et al. |
| 5,797,949 A | 8/1998 | Parodi |
| 5,799,655 A | 9/1998 | Jang et al. |
| 5,807,329 A | 9/1998 | Gelman |
| 5,807,340 A | 9/1998 | Pokras |
| 5,810,867 A | 9/1998 | Zarbatany et al. |
| 5,816,923 A | 10/1998 | Milo et al. |
| 5,820,592 A | 10/1998 | Hammerslag |
| 5,823,971 A | 10/1998 | Robinson et al. |
| 5,824,039 A | 10/1998 | Piplani et al. |
| 5,824,055 A | 10/1998 | Spiridigliozzi et al. |
| 5,827,201 A | 10/1998 | Samson et al. |
| 5,827,229 A | 10/1998 | Auth et al. |
| 5,827,304 A | 10/1998 | Hart |
| 5,827,322 A | 10/1998 | Williams |
| 5,830,224 A | 11/1998 | Cohn et al. |
| 5,836,957 A | 11/1998 | Schulz et al. |
| 5,843,022 A | 12/1998 | Willard et al. |
| 5,843,103 A | 12/1998 | Wulfman |
| 5,843,161 A | 12/1998 | Solovay |
| 5,855,563 A | 1/1999 | Kaplan et al. |
| 5,865,748 A | 2/1999 | Co et al. |
| 5,868,685 A | 2/1999 | Powell et al. |
| 5,868,767 A | 2/1999 | Farley et al. |
| 5,871,536 A | 2/1999 | Lazarus |
| 5,873,882 A | 2/1999 | Straub et al. |
| 5,876,414 A | 3/1999 | Straub |
| 5,879,397 A | 3/1999 | Kalberer et al. |
| 5,882,589 A | 3/1999 | Mariotti |
| 5,883,458 A | 3/1999 | Sumita et al. |
| 5,888,201 A | 3/1999 | Stinson et al. |
| 5,895,399 A | 4/1999 | Barbut et al. |
| 5,895,402 A | 4/1999 | Hundertmark et al. |
| 5,902,245 A | 5/1999 | Yock |
| 5,910,150 A | 6/1999 | Saadat |
| 5,911,734 A | 6/1999 | Tsugita et al. |
| 5,916,210 A | 6/1999 | Winston |
| 5,922,003 A | 7/1999 | Anctil et al. |
| 5,935,108 A | 8/1999 | Katoh et al. |
| 5,938,645 A | 8/1999 | Gordon |
| 5,938,671 A | 8/1999 | Katoh et al. |
| 5,938,672 A | 8/1999 | Nash |
| 5,941,869 A | 8/1999 | Patterson et al. |
| 5,947,985 A | 9/1999 | Imran |
| 5,948,184 A | 9/1999 | Frantzen et al. |
| 5,951,480 A | 9/1999 | White et al. |
| 5,951,482 A | 9/1999 | Winston et al. |
| 5,954,745 A | 9/1999 | Gertler et al. |
| 5,968,064 A | 10/1999 | Selmon et al. |
| 5,972,019 A | 10/1999 | Engelson et al. |
| 5,979,951 A | 11/1999 | Shimura |
| 5,985,397 A | 11/1999 | Witt et al. |
| 5,989,281 A | 11/1999 | Barbut et al. |
| 5,997,557 A | 12/1999 | Barbut et al. |
| 6,001,112 A | 12/1999 | Taylor |
| 6,010,449 A | 1/2000 | Selmon et al. |
| 6,010,522 A | 1/2000 | Barbut et al. |
| 6,013,072 A | 1/2000 | Winston et al. |
| 6,016,649 A | 1/2000 | Bock et al. |
| 6,019,778 A | 2/2000 | Wilson et al. |
| 6,022,362 A | 2/2000 | Lee et al. |
| 6,027,450 A | 2/2000 | Brown et al. |
| 6,027,460 A | 2/2000 | Shturman |
| 6,027,514 A | 2/2000 | Stine et al. |
| 6,032,673 A | 3/2000 | Savage et al. |
| 6,036,646 A | 3/2000 | Barthe et al. |
| 6,036,656 A | 3/2000 | Slater |
| 6,036,707 A | 3/2000 | Spaulding |
| 6,039,693 A | 3/2000 | Seward et al. |
| 6,048,349 A | 4/2000 | Winston et al. |
| 6,050,949 A | 4/2000 | White et al. |
| 6,063,093 A | 5/2000 | Winston et al. |
| 6,066,153 A | 5/2000 | Lev |
| 6,068,603 A | 5/2000 | Suzuki |
| 6,068,638 A | 5/2000 | Makower |
| 6,081,738 A | 6/2000 | Hinohara et al. |
| RE36,764 E | 7/2000 | Zacca et al. |
| 6,095,990 A | 8/2000 | Parodi |
| 6,099,542 A | 8/2000 | Cohn et al. |
| 6,106,515 A | 8/2000 | Winston et al. |
| 6,110,121 A | 8/2000 | Lenker |
| 6,120,515 A | 9/2000 | Rogers et al. |
| 6,120,516 A | 9/2000 | Selmon et al. |
| 6,126,649 A | 10/2000 | VanTassel et al. |
| 6,129,734 A | 10/2000 | Shturman et al. |
| 6,134,003 A | 10/2000 | Tearney et al. |
| 6,152,909 A | 11/2000 | Bagaoisan et al. |
| 6,152,938 A | 11/2000 | Curry |
| 6,156,046 A | 12/2000 | Passafaro et al. |
| 6,157,852 A | 12/2000 | Selmon et al. |
| 6,159,195 A | 12/2000 | Ha et al. |
| 6,159,225 A | 12/2000 | Makower |
| 6,165,127 A | 12/2000 | Crowley |
| 6,179,859 B1 | 1/2001 | Bates et al. |
| 6,183,432 B1 | 2/2001 | Milo |
| 6,187,025 B1 | 2/2001 | Machek |
| 6,190,353 B1 | 2/2001 | Makower et al. |
| 6,191,862 B1 | 2/2001 | Swanson et al. |
| 6,193,676 B1 | 2/2001 | Winston et al. |
| 6,196,963 B1 | 3/2001 | Williams |
| 6,206,898 B1 | 3/2001 | Honeycutt et al. |
| 6,217,527 B1 | 4/2001 | Selmon et al. |
| 6,217,549 B1 | 4/2001 | Selmon et al. |
| 6,217,595 B1 | 4/2001 | Shturman et al. |
| 6,221,049 B1 | 4/2001 | Selmon et al. |

(56) References Cited

U.S. PATENT DOCUMENTS

| | | |
|---|---|---|
| 6,221,332 B1 | 4/2001 | Thumm et al. |
| 6,228,049 B1 | 5/2001 | Schroeder et al. |
| 6,228,076 B1 | 5/2001 | Winston et al. |
| 6,231,546 B1 | 5/2001 | Milo et al. |
| 6,231,549 B1 | 5/2001 | Noecker et al. |
| 6,235,000 B1 | 5/2001 | Milo et al. |
| 6,238,405 B1 | 5/2001 | Findlay, III et al. |
| 6,241,667 B1 | 6/2001 | Vetter et al. |
| 6,241,744 B1 | 6/2001 | Imran et al. |
| 6,245,012 B1 | 6/2001 | Kleshinski |
| 6,258,052 B1 | 7/2001 | Milo |
| 6,263,236 B1 | 7/2001 | Kasinkas et al. |
| 6,264,611 B1 | 7/2001 | Ishikawa et al. |
| 6,266,550 B1 | 7/2001 | Selmon et al. |
| 6,277,138 B1 | 8/2001 | Levinson et al. |
| 6,283,951 B1 | 9/2001 | Flaherty et al. |
| 6,283,983 B1 | 9/2001 | Makower et al. |
| 6,299,622 B1 | 10/2001 | Snow et al. |
| 6,299,623 B1 | 10/2001 | Wulfman |
| 6,302,875 B1 | 10/2001 | Makower et al. |
| 6,305,834 B1 | 10/2001 | Schubert et al. |
| 6,312,444 B1 | 11/2001 | Barbut |
| 6,319,242 B1 | 11/2001 | Patterson et al. |
| 6,319,275 B1 | 11/2001 | Lashinski et al. |
| 6,330,884 B1 | 12/2001 | Kim |
| 6,355,005 B1 | 3/2002 | Powell et al. |
| 6,361,545 B1 | 3/2002 | Macoviak et al. |
| 6,375,615 B1 | 4/2002 | Flaherty et al. |
| 6,383,195 B1 | 5/2002 | Richard |
| 6,383,205 B1 | 5/2002 | Samson et al. |
| 6,394,976 B1 | 5/2002 | Winston et al. |
| 6,398,798 B2 | 6/2002 | Selmon et al. |
| 6,422,736 B1 | 7/2002 | Antoniades et al. |
| 6,423,081 B1 | 7/2002 | Lee et al. |
| 6,425,870 B1 | 7/2002 | Flesch |
| 6,428,551 B1 | 8/2002 | Hall et al. |
| 6,428,552 B1 | 8/2002 | Sparks |
| 6,443,966 B1 | 9/2002 | Shiu |
| 6,445,939 B1 | 9/2002 | Swanson et al. |
| 6,447,525 B2 | 9/2002 | Follmer et al. |
| 6,451,036 B1 | 9/2002 | Heitzmann et al. |
| 6,454,779 B1 | 9/2002 | Taylor |
| 6,475,226 B1 | 11/2002 | Belef et al. |
| 6,482,217 B1 | 11/2002 | Pintor et al. |
| 6,497,711 B1 | 12/2002 | Plaia et al. |
| 6,501,551 B1 | 12/2002 | Tearney et al. |
| 6,520,975 B2 | 2/2003 | Branco |
| RE38,018 E | 3/2003 | Anctil et al. |
| 6,532,380 B1 | 3/2003 | Close et al. |
| 6,533,749 B1 | 3/2003 | Mitusina et al. |
| 6,561,998 B1 | 5/2003 | Roth et al. |
| 6,565,588 B1 | 5/2003 | Clement et al. |
| 6,569,177 B1 | 5/2003 | Dillard et al. |
| 6,592,526 B1 | 7/2003 | Lenker |
| 6,620,180 B1 | 9/2003 | Bays et al. |
| 6,623,437 B2 | 9/2003 | Hinchliffe et al. |
| 6,623,495 B2 | 9/2003 | Findlay, III et al. |
| 6,623,496 B2 | 9/2003 | Snow et al. |
| 6,629,953 B1 | 10/2003 | Boyd |
| 6,638,233 B2 | 10/2003 | Corvi et al. |
| RE38,335 E | 11/2003 | Aust et al. |
| 6,652,505 B1 | 11/2003 | Tsugita |
| 6,652,548 B2 | 11/2003 | Evans et al. |
| 6,656,195 B2 | 12/2003 | Peters et al. |
| 6,666,874 B2 | 12/2003 | Heitzmann et al. |
| 6,682,543 B2 | 1/2004 | Barbut et al. |
| 6,733,511 B2 | 5/2004 | Hall et al. |
| 6,740,103 B2 | 5/2004 | Hall et al. |
| 6,746,462 B1 | 6/2004 | Selmon et al. |
| 6,764,495 B2 | 7/2004 | Lee et al. |
| 6,790,204 B2 | 9/2004 | Zadno-Azizi et al. |
| 6,790,215 B2 | 9/2004 | Findlay, III et al. |
| 6,818,001 B2 | 11/2004 | Wulfman et al. |
| 6,830,577 B2 | 12/2004 | Nash et al. |
| 6,843,797 B2 | 1/2005 | Nash et al. |
| 6,849,068 B1 | 2/2005 | Bagaoisan et al. |
| 6,863,676 B2 | 3/2005 | Lee et al. |
| 6,911,026 B1 | 6/2005 | Hall et al. |
| 6,919,057 B2 * | 7/2005 | Halstead ............... A61B 1/123 422/1 |
| 6,970,732 B2 | 11/2005 | Winston et al. |
| 6,997,934 B2 | 2/2006 | Snow et al. |
| 7,153,315 B2 | 12/2006 | Miller |
| 7,172,610 B2 | 2/2007 | Heitzmann et al. |
| 7,208,511 B2 | 4/2007 | Williams et al. |
| 7,235,088 B2 | 6/2007 | Pintor et al. |
| 7,318,831 B2 | 1/2008 | Alvarez et al. |
| 7,388,495 B2 | 6/2008 | Fallin et al. |
| 7,479,148 B2 | 1/2009 | Beaupre |
| 7,488,322 B2 | 2/2009 | Brunnett et al. |
| 7,524,289 B2 | 4/2009 | Lenker |
| 7,603,166 B2 | 10/2009 | Casscells, III et al. |
| 7,708,749 B2 | 5/2010 | Simpson et al. |
| 7,713,235 B2 | 5/2010 | Torrance et al. |
| 7,713,279 B2 | 5/2010 | Simpson et al. |
| 7,729,745 B2 | 6/2010 | Maschke |
| 7,734,332 B2 | 6/2010 | Sher |
| 7,753,852 B2 | 7/2010 | Maschke |
| 7,758,599 B2 | 7/2010 | Snow et al. |
| 7,771,444 B2 | 8/2010 | Patel et al. |
| 7,887,556 B2 | 2/2011 | Simpson et al. |
| 8,226,674 B2 | 7/2012 | Simpson et al. |
| 9,579,157 B2 * | 2/2017 | Moberg ............... A61B 90/70 |
| 2001/0000041 A1 | 3/2001 | Selmon et al. |
| 2001/0031784 A1 | 10/2001 | Petersen et al. |
| 2001/0031981 A1 | 10/2001 | Evans et al. |
| 2001/0044622 A1 | 11/2001 | Vardi et al. |
| 2001/0049500 A1 | 12/2001 | VanTassel et al. |
| 2002/0019644 A1 | 2/2002 | Hastings et al. |
| 2002/0022788 A1 | 2/2002 | Corvi et al. |
| 2002/0058904 A1 | 5/2002 | Boock et al. |
| 2002/0077373 A1 | 6/2002 | Hudson et al. |
| 2002/0077642 A1 | 6/2002 | Patel et al. |
| 2002/0095141 A1 | 7/2002 | Belef et al. |
| 2002/0103459 A1 | 8/2002 | Sparks et al. |
| 2002/0177800 A1 | 11/2002 | Bagaoisan et al. |
| 2002/0188307 A1 | 12/2002 | Pintor et al. |
| 2003/0018346 A1 | 1/2003 | Follmer et al. |
| 2003/0023263 A1 | 1/2003 | Krolik et al. |
| 2003/0093098 A1 | 5/2003 | Heitzmann et al. |
| 2003/0120295 A1 | 6/2003 | Simpson et al. |
| 2003/0125757 A1 | 7/2003 | Patel et al. |
| 2003/0125758 A1 | 7/2003 | Simpson et al. |
| 2003/0163126 A1 | 8/2003 | West, Jr. |
| 2003/0199747 A1 | 10/2003 | Michlitsch et al. |
| 2003/0206484 A1 | 11/2003 | Childers et al. |
| 2003/0229369 A1 | 12/2003 | Findlay, III et al. |
| 2004/0006358 A1 | 1/2004 | Wulfman et al. |
| 2004/0049225 A1 | 3/2004 | Denison |
| 2004/0167553 A1 | 8/2004 | Simpson et al. |
| 2004/0167554 A1 | 8/2004 | Simpson et al. |
| 2004/0193034 A1 | 9/2004 | Wasicek et al. |
| 2004/0210245 A1 | 10/2004 | Erickson et al. |
| 2005/0004585 A1 | 1/2005 | Hall et al. |
| 2005/0004594 A1 | 1/2005 | Nool et al. |
| 2005/0021063 A1 | 1/2005 | Hall et al. |
| 2005/0042239 A1 | 2/2005 | Lipiecki et al. |
| 2005/0090845 A1 | 4/2005 | Boyd |
| 2005/0090849 A1 | 4/2005 | Adams |
| 2005/0177068 A1 | 8/2005 | Simpson |
| 2005/0191222 A1 | 9/2005 | Lin et al. |
| 2005/0216018 A1 | 9/2005 | Sennett |
| 2005/0222596 A1 | 10/2005 | Maschke |
| 2005/0222663 A1 | 10/2005 | Simpson et al. |
| 2006/0015126 A1 | 1/2006 | Sher |
| 2006/0235334 A1 | 10/2006 | Corvi et al. |
| 2006/0259052 A1 | 11/2006 | Pintor et al. |
| 2007/0010840 A1 | 1/2007 | Rosenthal et al. |
| 2007/0038061 A1 | 2/2007 | Huennekens et al. |
| 2007/0049958 A1 | 3/2007 | Adams |
| 2007/0135712 A1 | 6/2007 | Maschke |
| 2007/0135886 A1 | 6/2007 | Maschke |
| 2007/0142785 A1 * | 6/2007 | Lundgaard ......... A61M 5/1418 604/179 |

(56) References Cited

U.S. PATENT DOCUMENTS

| | | | |
|---|---|---|---|
| 2007/0167824 A1 | 7/2007 | Lee et al. |
| 2007/0225739 A1 | 9/2007 | Pintor et al. |
| 2007/0265647 A1 | 11/2007 | Bonnette et al. |
| 2007/0276419 A1 | 11/2007 | Rosenthal |
| 2008/0001643 A1 | 1/2008 | Lee |
| 2008/0004644 A1 | 1/2008 | To et al. |
| 2008/0004645 A1 | 1/2008 | To et al. |
| 2008/0004646 A1 | 1/2008 | To et al. |
| 2008/0004647 A1 | 1/2008 | To et al. |
| 2008/0045986 A1 | 2/2008 | To et al. |
| 2008/0051812 A1 | 2/2008 | Schmitz et al. |
| 2008/0065124 A1 | 3/2008 | Olson |
| 2008/0065125 A1 | 3/2008 | Olson |
| 2008/0097403 A1 | 4/2008 | Donaldson et al. |
| 2008/0125799 A1 | 5/2008 | Adams |
| 2008/0161840 A1 | 7/2008 | Osiroff et al. |
| 2008/0177139 A1 | 7/2008 | Courtney et al. |
| 2008/0208227 A1 | 8/2008 | Kadykowski et al. |
| 2008/0249553 A1 | 10/2008 | Gruber et al. |
| 2008/0312673 A1 | 12/2008 | Viswanathan et al. |
| 2009/0012548 A1 | 1/2009 | Thatcher et al. |
| 2009/0018565 A1 | 1/2009 | To et al. |
| 2009/0018566 A1 | 1/2009 | Escudero et al. |
| 2009/0138031 A1 | 5/2009 | Tsukernik |
| 2009/0187203 A1 | 7/2009 | Corvi et al. |
| 2009/0216125 A1 | 8/2009 | Lenker |
| 2009/0216180 A1 | 8/2009 | Lee et al. |
| 2009/0226063 A1 | 9/2009 | Rangwala et al. |
| 2009/0234378 A1 | 9/2009 | Escudero et al. |
| 2009/0270888 A1 | 10/2009 | Patel et al. |
| 2009/0275966 A1 | 11/2009 | Mitusina |
| 2009/0299394 A1 | 12/2009 | Simpson et al. |
| 2009/0306689 A1 | 12/2009 | Welty et al. |
| 2010/0030216 A1 | 2/2010 | Arcenio |
| 2010/0049225 A1 | 2/2010 | To et al. |
| 2010/0130996 A1 | 5/2010 | Doud et al. |
| 2010/0198240 A1 | 8/2010 | Simpson et al. |
| 2010/0241147 A1 | 9/2010 | Maschke |
| 2010/0280534 A1 | 11/2010 | Sher |
| 2010/0292721 A1 | 11/2010 | Moberg |
| 2010/0298850 A1 | 11/2010 | Snow et al. |
| 2010/0312263 A1 | 12/2010 | Moberg et al. |
| 2011/0004107 A1 | 1/2011 | Rosenthal et al. |
| 2011/0022069 A1 | 1/2011 | Mitusina |
| 2011/0040315 A1 | 2/2011 | To et al. |
| 2011/0130777 A1 | 6/2011 | Zhang et al. |
| 2011/0144673 A1 | 6/2011 | Zhang et al. |
| 2012/0330336 A1 | 12/2012 | Simpson et al. |
| 2015/0090620 A1 | 4/2015 | Seitz, III |

FOREIGN PATENT DOCUMENTS

| | | |
|---|---|---|
| DE | 3732236 C1 | 9/1987 |
| DE | 8900059 | 1/1989 |
| DE | 9303531.4 | 3/1993 |
| DE | 4444166 A1 | 6/1996 |
| DE | 29722136 U1 | 4/1999 |
| EP | 0 086 048 A2 | 8/1983 |
| EP | 0 107 009 A2 | 5/1984 |
| EP | 0 229 620 A2 | 7/1987 |
| EP | 0 291 170 A1 | 11/1988 |
| EP | 0 302 701 A2 | 2/1989 |
| EP | 0 330 843 A1 | 9/1989 |
| EP | 0 373 927 A2 | 6/1990 |
| EP | 0 421 457 A1 | 4/1991 |
| EP | 0 431 752 A2 | 6/1991 |
| EP | 0 448 859 A2 | 10/1991 |
| EP | 0 463 798 A1 | 1/1992 |
| EP | 0 490 565 A1 | 6/1992 |
| EP | 0 514 810 A1 | 11/1992 |
| EP | 0 526 042 A1 | 2/1993 |
| EP | 0 533 320 A2 | 3/1993 |
| EP | 0 608 911 A1 | 8/1994 |
| EP | 0 608 912 A1 | 8/1994 |
| EP | 0 611 522 A1 | 8/1994 |
| EP | 0 648 414 A2 | 4/1995 |
| EP | 0 657 140 A1 | 6/1995 |
| EP | 0 680 695 A2 | 11/1995 |
| EP | 0 983 749 A2 | 3/2000 |
| EP | 1 767 159 A1 | 3/2007 |
| EP | 1 875 871 A2 | 1/2008 |
| GB | 2 093 353 A | 9/1982 |
| GB | 2 115 829 A | 9/1983 |
| GB | 2 210 965 A | 6/1989 |
| JP | 2-206452 | 8/1990 |
| JP | 2-271847 | 11/1990 |
| JP | 3-186256 | 8/1991 |
| JP | 04-200459 | 7/1992 |
| JP | 05-042162 | 2/1993 |
| JP | 05-056984 | 3/1993 |
| JP | 5184679 A | 7/1993 |
| JP | 6-269460 | 9/1994 |
| JP | 7-75611 | 8/1995 |
| SU | 442795 | 9/1974 |
| SU | 665908 | 6/1979 |
| WO | 89/06517 | 7/1989 |
| WO | 9207500 | 5/1992 |
| WO | 93/13716 | 7/1993 |
| WO | 93/13717 | 7/1993 |
| WO | 93/16642 | 9/1993 |
| WO | 95/21576 | 8/1995 |
| WO | 96/11648 | 4/1996 |
| WO | 97/46164 | 12/1997 |
| WO | 98/04199 | 2/1998 |
| WO | 98/24372 | 6/1998 |
| WO | 99/39648 | 8/1999 |
| WO | 99/52454 | 10/1999 |
| WO | 02/16017 A2 | 2/2000 |
| WO | 00/30531 | 6/2000 |
| WO | 00/54735 | 9/2000 |
| WO | 00/62913 | 10/2000 |
| WO | 00/68300 | 11/2000 |
| WO | 00/72955 A1 | 12/2000 |
| WO | 01/15609 A1 | 3/2001 |
| WO | 01/19444 A1 | 3/2001 |
| WO | 01/30433 A1 | 5/2001 |
| WO | 01/43809 A1 | 6/2001 |
| WO | 01/43857 A1 | 6/2001 |
| WO | 02/45598 A2 | 6/2002 |
| WO | 2006/058223 A2 | 6/2006 |
| WO | 2006/066012 A2 | 6/2006 |

OTHER PUBLICATIONS

Judkins Left Coronary Catheter, posted: Feb. 19, 2009, [online], [retrieved on Mar. 29, 2011], retrieved from the Cardiophile MD using Internet website <URL:http://cardiophile.org/2009/02/judkins-left-coronary-catheter.html> (3 pages).

Huang et al., "Optical Coherence Tomography," Science, 254: 1178-1181 (1991).

Brezinski et al., "Optical Coherence Tomography for Optical Biopsy," Circulation, 93: 1206-1213 (1996).

Brezinski et al., "Assessing Atherosclerotic Plaque Morphology: Comparison of Optical Coherence Tomography and High Frequency Intravascular Ultrasound," Heart, 77:397-403 (1997).

\* cited by examiner

CLEANING DEVICE FOR MEDICAL INSTRUMENT AND METHOD OF USE

CROSS-REFERENCE TO RELATED APPLICATION

The present application is a continuation of U.S. application Ser. No. 14/026,009, filed Sep. 13, 2013, which claims the benefit of U.S. Provisional Application Ser. No. 61/700,636, filed Sep. 13, 2012, the entirety of which is hereby incorporated by reference.

FIELD OF THE DISCLOSURE

The present invention relates to a cleaning device for cleaning a medical instrument. More particularly, this invention relates to a cleaning device capable of cleaning residual matter from a distal end portion of a catheter.

BACKGROUND OF THE DISCLOSURE

Medical instruments, including those used in surgical or intravascular procedures require cleaning to remove matter such as plaque, calcium, blood, tissue, and other luminal debris in an effective, efficient and timely manner. However, some medical devices, including catheters, can be difficult to clean quickly and efficiently because of their size and construction.

SUMMARY OF THE DISCLOSURE

Various embodiments of cleaning devices and their methods of use are disclosed. Distinguishing features that may be included in these cleaning devices and methods are described below. It is intended that the cleaning devices and methods may include one or more of these features individually or in combination and it is not intended that the cleaning devices or the methods of use be limited to the specific embodiments described herein.

In one aspect, a cleaning device includes a flushing chamber having opposite proximal and distal ends, and a length extending between the proximal and distal ends. An inlet port of the cleaning device is in fluid communication with the flushing chamber and configured for fluid connection to a source of fluid. The flushing chamber is selectively openable along its length to an open position, in which the distal end portion of the medical instrument is insertable into the flushing chamber, and selectively closable along its length to a closed position, in which the distal end portion of the medical instrument is enclosed and fluidly sealed within the flushing chamber.

BRIEF DESCRIPTION OF THE DRAWINGS

Corresponding reference characters indicate corresponding parts throughout the drawings.

DETAILED DESCRIPTION OF THE DISCLOSURE

Described herein are embodiments of a device and method for cleaning and flushing residual matter from a medical device including but not limited to an intraluminal surgical device including a catheter. Although the various embodiments of the cleaning device are described herein for use in cleaning catheters having catheter bodies adapted for intraluminal introduction the devices may also be used to clean other intraluminal surgical devices or other medical devices of a general nature. In other words, it is not intended that the use of the embodiments described herein be limited to cleaning intraluminal catheters. The dimensions and other physical characteristics of the cleaning device may vary significantly depending on the size and/or physical characteristics of the catheter, surgical instrument, or other medical device to be cleaned.

Figure 1:
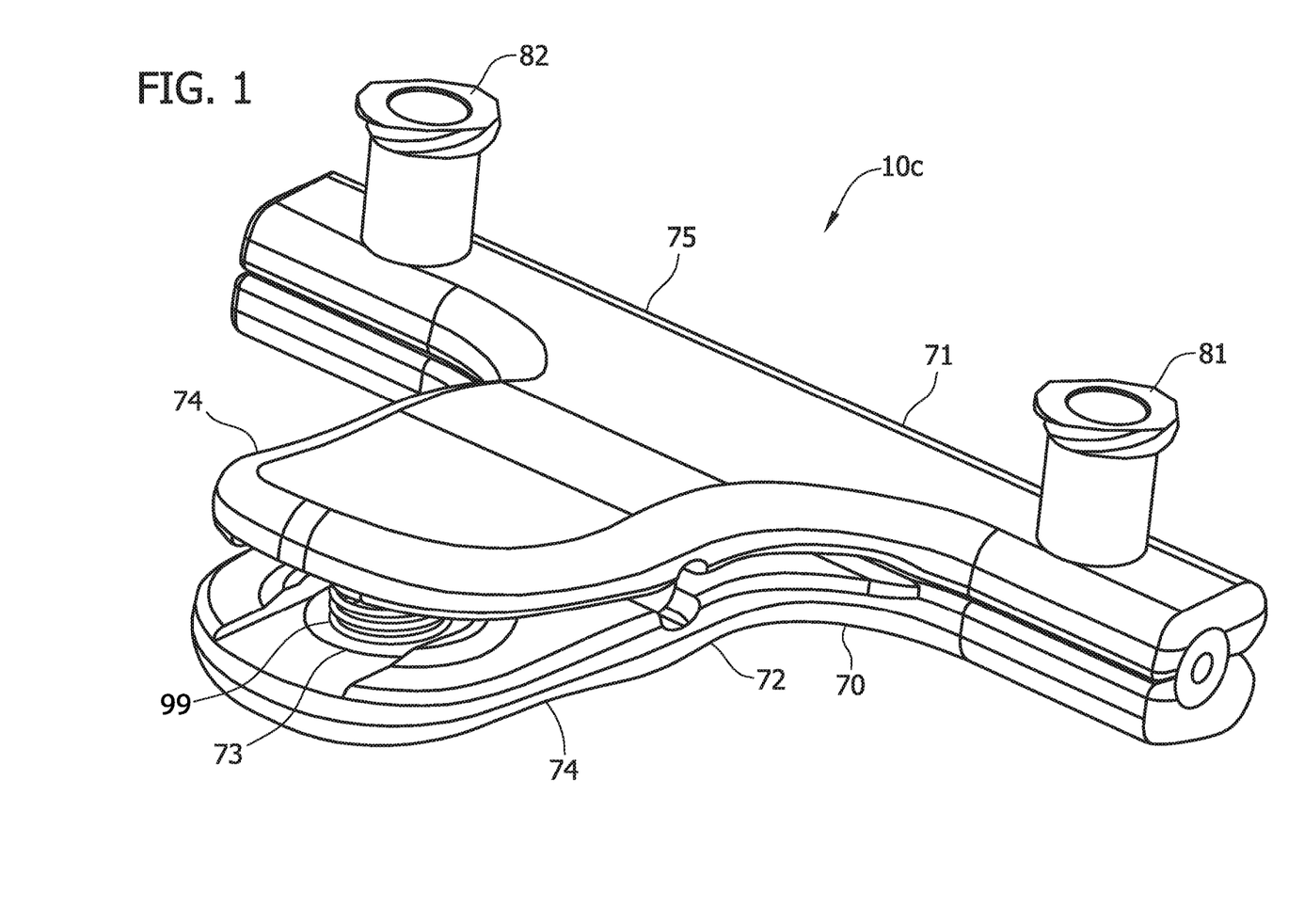
FIG. 1 is a perspective of a first embodiment of a cleaning device for a medical instrument.
Figure 2:
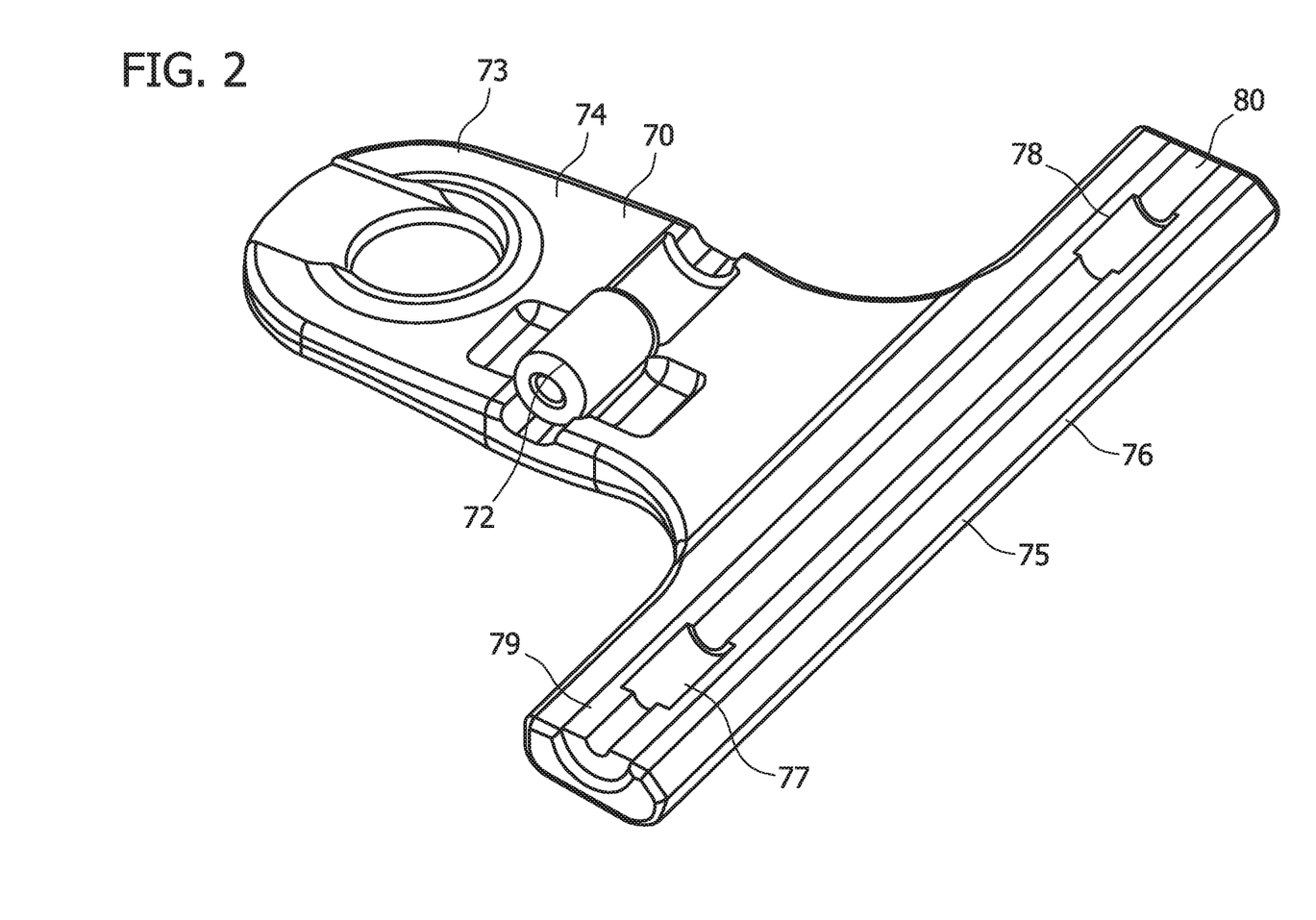
FIG. 2 is a perspective of a lower half of the cleaning device of FIG. 1, an upper half of the cleaning device being removed.
Figure 3:
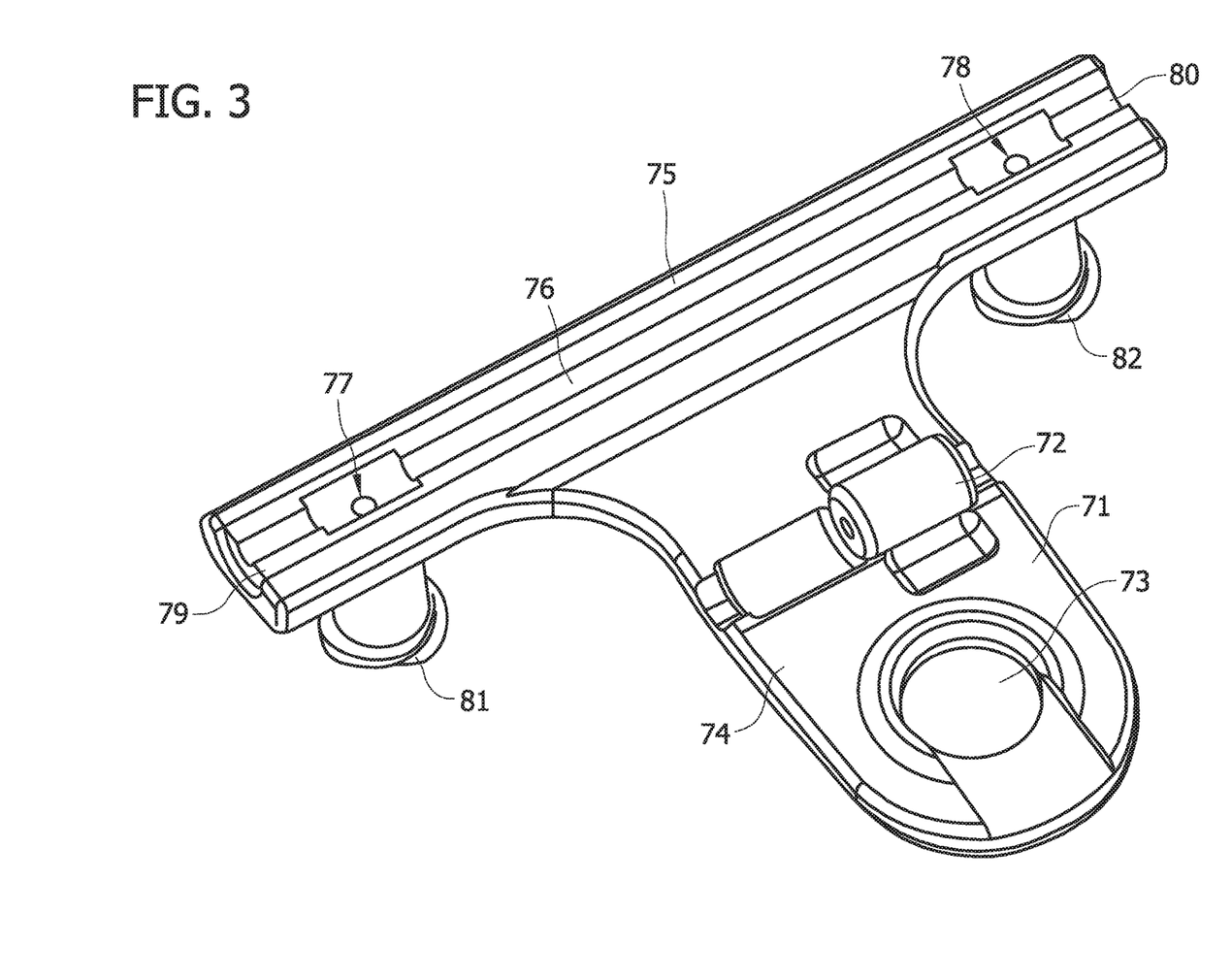
FIG. 3 is a perspective of the upper half of the cleaning device of FIG. 1, the lower half of the cleaning device being removed.

FIGS. 1-3 illustrate an embodiment of cleaning device, generally indicated at 10c. Cleaning device 10c has lower half 70 coupled to upper half 71 by hinge 72. Hinge 72 is not limiting and could be any suitable structure or system for coupling lower half 70 to upper half 71. Lower half 70 and upper half 71 may be made from any suitable material and may be, for example, made from a rigid thermoplastic material. Lower half 70 and upper half 71 each have a spring seat or depression 73 in handle portion 74 that accepts a spring 99 (illustrated schematically). Lower half 70 and upper half 71 each have luminal portion 75 that is perpendicular to handle portion 74. During use luminal portions 75 combine to form a flushing chamber or lumen 76 that has inlet cavity 77, outlet cavity 78, seal 79 and stop 80. Lumen 76 may be made from any suitable material and may, for example, be made from silicone or could be a TPR overmold.

Upper half 71 has inlet port 81 coupled to the outer surface of luminal portion 75. Inlet port 81 is connected to inlet cavity 77 of flushing chamber or lumen 76 to allow the flow of a fluid or a gas into the cavity. Upper half 71 may also have outlet port 82 coupled to the outer surface of luminal portion 75. Outlet port 82 is connected to outlet cavity 78 of flushing chamber or lumen 76 to allow the flow of fluid or a gas from the outlet cavity 78 through outlet port 82. Catheter C is inserted into cleaning device 10c by compressing, pinching or squeezing handle portion 74 of upper half 71 and handle portion 74 of lower half 70 separating luminal portion 75 of upper half 71 from luminal portion 75 of lower half 70. The distal end of catheter C is then placed within flushing chamber 76. The handle portions are then released to allow the spring force to cause the upper half 71 and lower half 70 to enclose the catheter. Luminal portions 75 of the upper half 71 and lower half 70 enclose and seal the distal tip of catheter C within flushing chamber or lumen 76 of cleaning device 10c.

Figure 4:
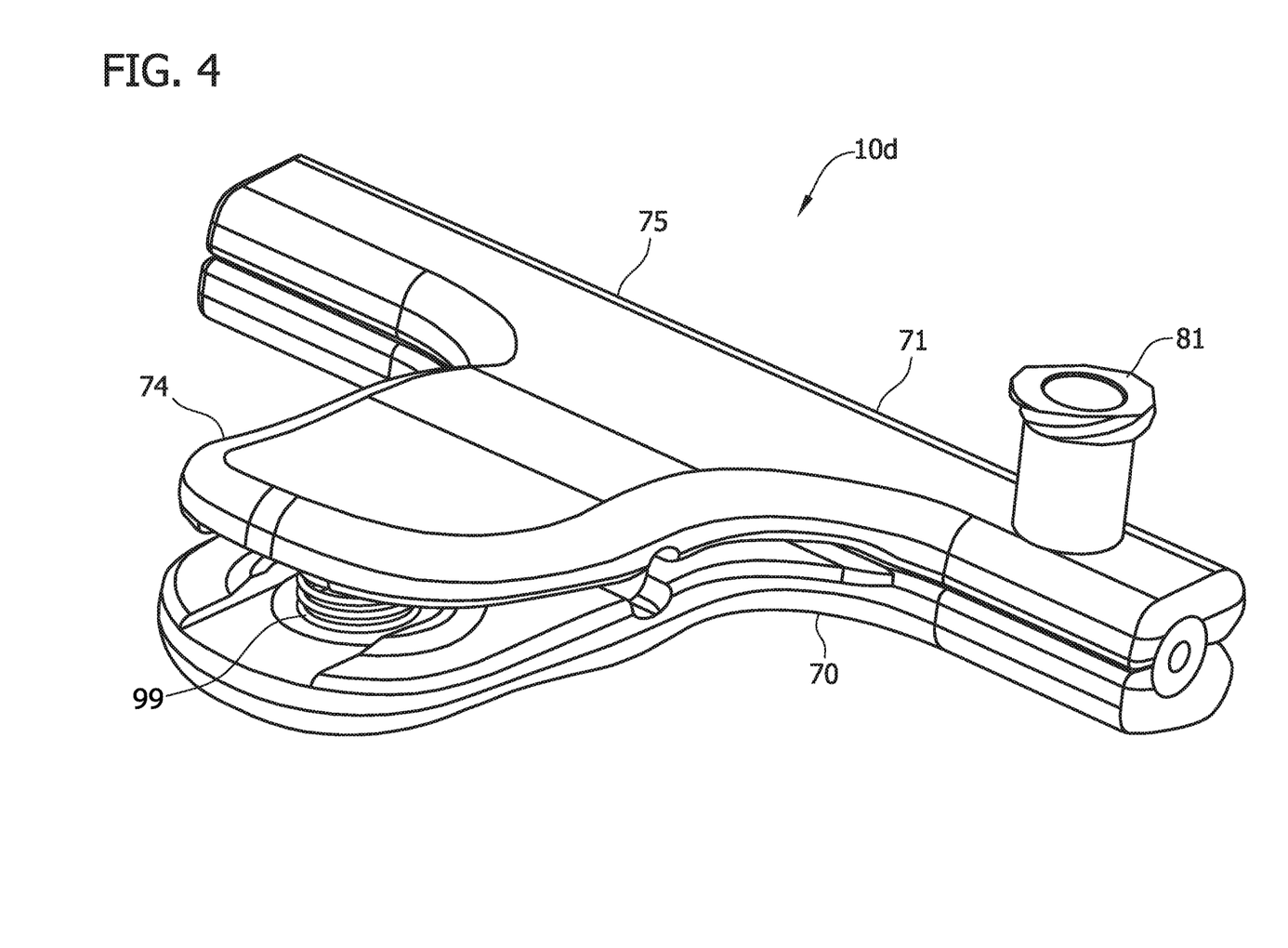
FIG. 4 is a perspective of a second embodiment of a cleaning device for a medical instrument.
Figure 5:
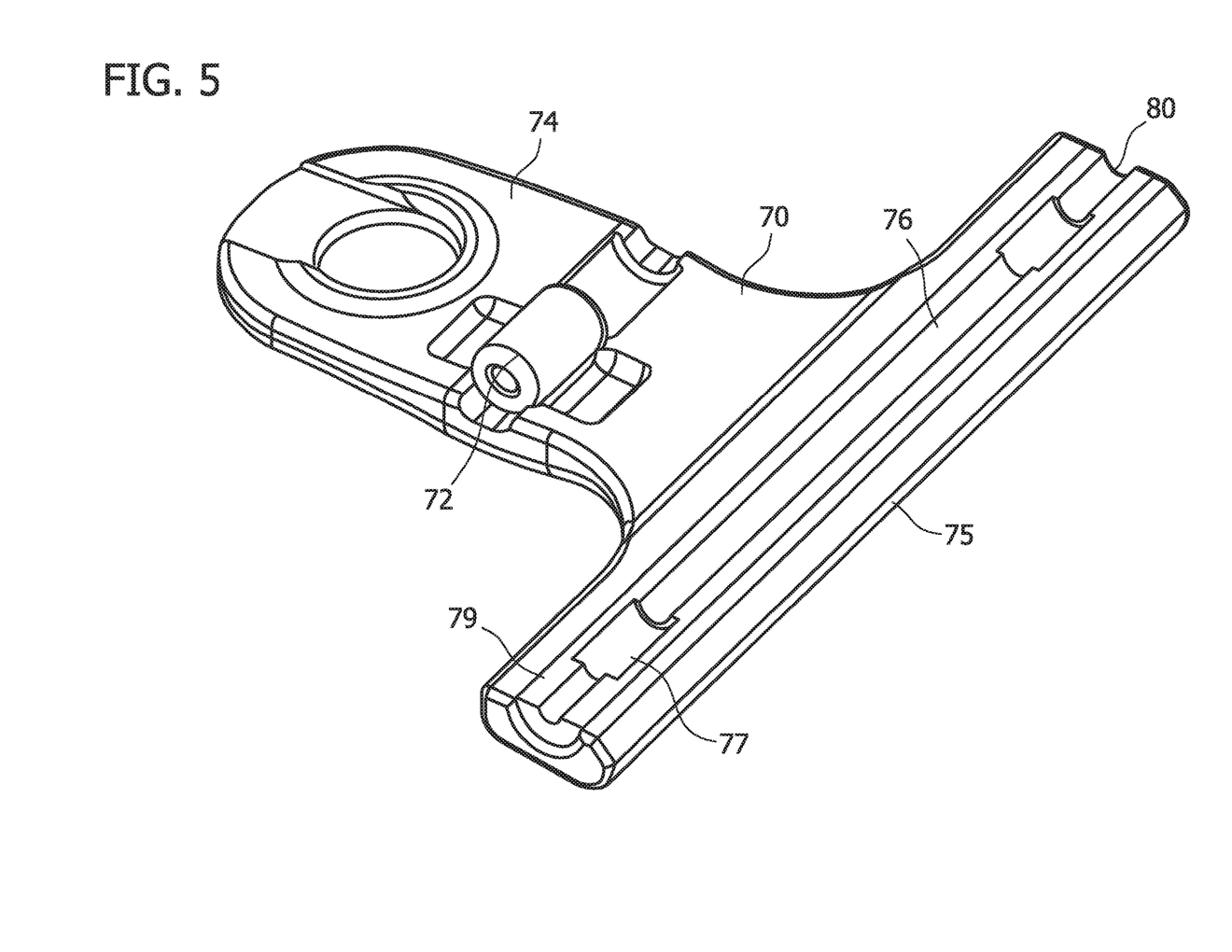
FIG. 5 is a perspective of a lower half of the cleaning device of FIG. 4, an upper half of the cleaning device being removed.
Figure 6:
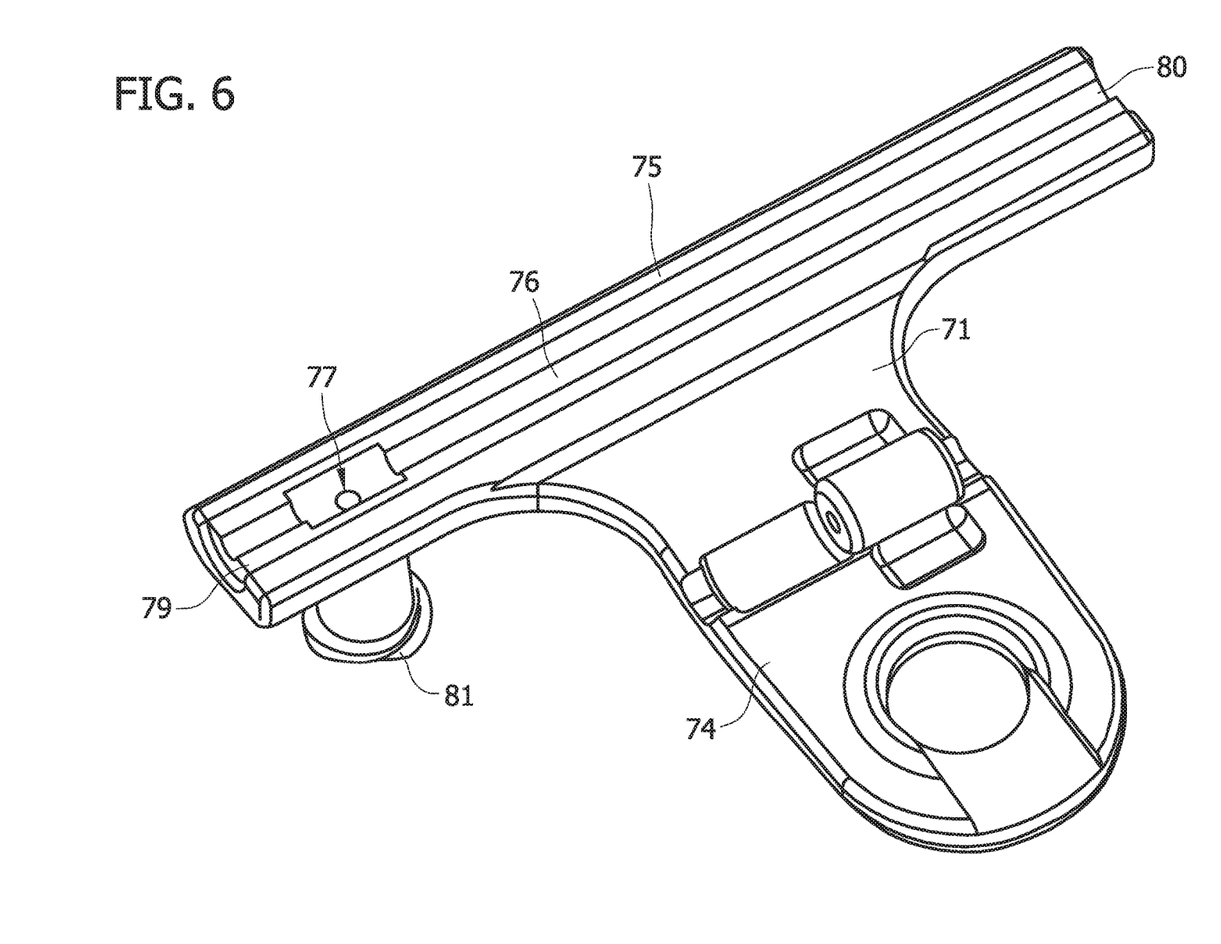
FIG. 6 is a perspective of the upper half of the cleaning device of FIG. 4, the lower half of the cleaning device being removed.

For catheters C' having one or more distal openings O positioned at or adjacent the distal end of the catheter the outlet port may be located directly adjacent the distal opening. FIGS. 4-6 illustrate cleaning device 10d which is substantially similar to cleaning device 10c except that outlet port 82 is replaced by outlet 83. Outlet 83 is positioned at a distal end of lumen 76. Catheter C' is inserted into cleaning device 10d by compressing, pinching or squeezing handle portion 74 of upper half 71 and handle portion 74 of lower half 70 separating luminal portion 75 of upper half 71 from luminal portion 75 of lower half 70. The distal end of catheter C' is then placed within flushing chamber 76 and the handle portions are released so that luminal portions 75 of the upper half 71 and lower half 70 enclose and seal the distal tip of catheter C' within flushing chamber or lumen 76 of cleaning device 10d.

Figure 7:
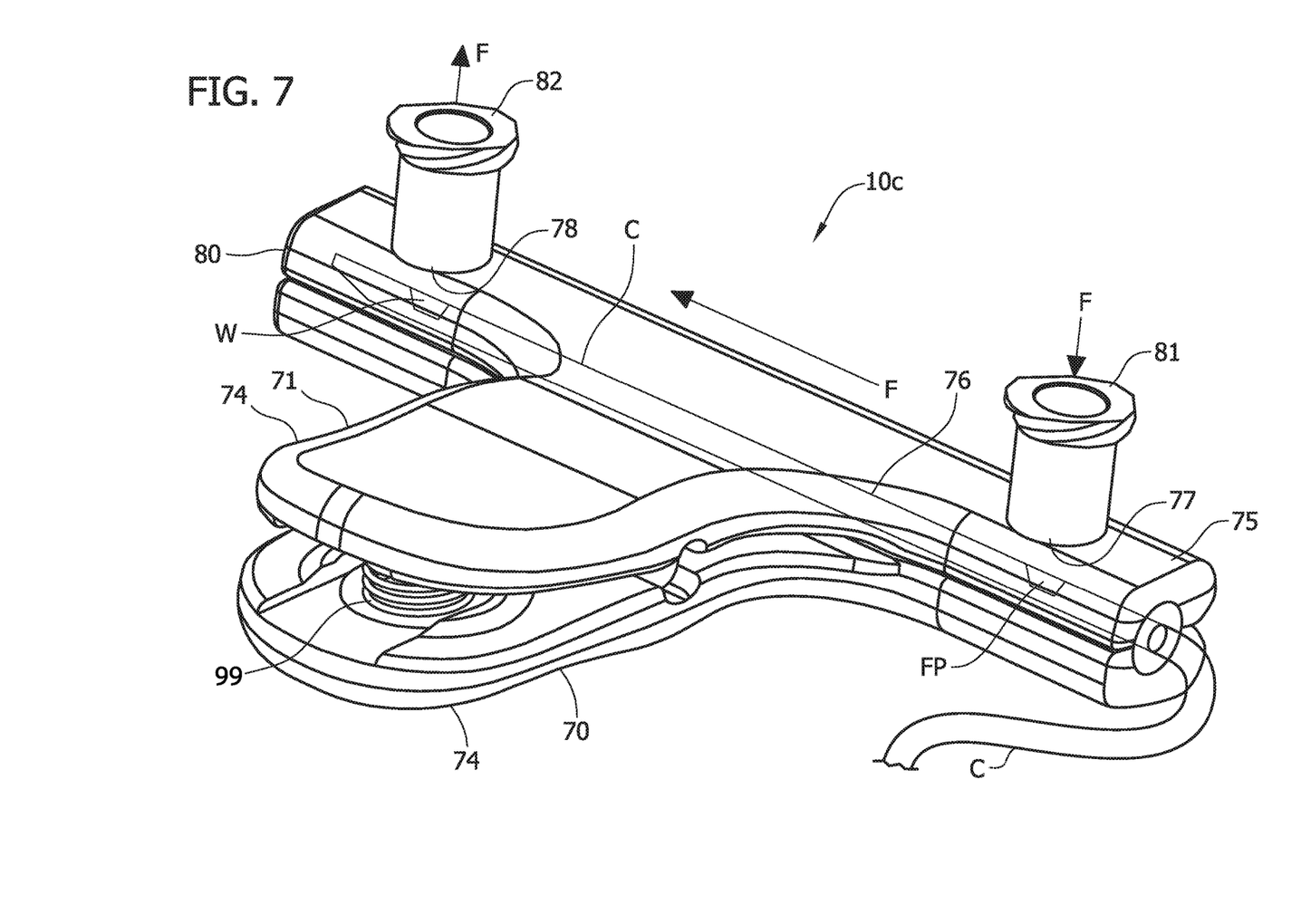
FIG. 7 is similar to FIG. 1, except the medical instrument is shown received in the cleaning device during a cleaning process.

FIG. 7 illustrates a method of using cleaning device 10c with a catheter C having a side cutting window W and a flush port FP, located proximal of the cutting window. Catheter C is inserted into cleaning device 10c by compressing, pinching or squeezing handle portion 74 of upper half 71 and handle portion 74 of lower half 70 separating luminal portion 75 of upper half 71 from luminal portion 75 of lower half 70. A distal end of catheter C is inserted into the flushing chamber or lumen 76 and positioned where the cutting window W is located within outlet cavity 78 and the flush port FP is located within inlet cavity 77.

Once catheter C has been inserted cutting window W may be aligned adjacently with outlet port 82 and flush port FP may be adjacently aligned with inlet port 81, although it should be understood that alignment of the openings and the ports are not required so long as fluid entering through the inlet port is caused to flow into the catheter through the flush port and out of the catheter through the cutting window W, as described below. The compression, pinching or squeezing of handle portions 74 of the upper half 71 and lower half 70 is halted and luminal portions 75 of the upper half 71 and lower half 70 enclose the distal tip of catheter C within flushing chamber or lumen 76 of cleaning device 10c. As the luminal portions 74 enclose the distal tip of catheter C, the elastic material of flush chamber or lumen 76 seals around the outer diameter of the catheter and assists in directing fluid flow through the lumen of catheter C. Seal 79 forms a seal about a proximal portion of the flushing chamber or lumen 76 and stop 80 forms a seal or stop at the distal end of the flush chamber or lumen 76, distal the catheter C.

Fluid F is then inserted into inlet port 81 flowing into the flush port FP of the catheter located within inlet cavity 77 of flush chamber 76, through an interior space in the catheter body and then out of the catheter body through the cutting window W located within outlet cavity 78 of flush chamber 76. The fluid then flows out of the flushing chamber through outlet port 82. Fluid F may be any suitable liquid and may specifically be water or saline. The fluid flow across and through the catheter dislodges and ejects matter such as plaque, calcium, tissue, cellular debris, blood, and other luminal debris from previous catheter use out of the cutting window W of the catheter and through outlet port 82. Fluid F may be caused to flow from the inlet port 81 to the outlet port 82 by introducing the fluid into the inlet port under pressure, by applying a vacuum at the outlet port 82 to create a negative pressure differential between the inlet and outlet ports, or a combination of both. The fluid F flowing through the catheter under pressure and/or suction will remove any unwanted debris or material from the catheter lumen or lumen.

It should also be pointed out that the cleaning device 10c could also be used with a catheter having a flush port FP which is distal to the cutting window W such as in a catheter having a collection chamber distal to the cutting window. In that case the catheter would be inserted such that the flush port FP is positioned within outlet cavity 78 and cutting window W is positioned within inlet cavity 77. The use is the same except that flow through the catheter is into the cutting window and out of the flush port FP.

Figure 8:
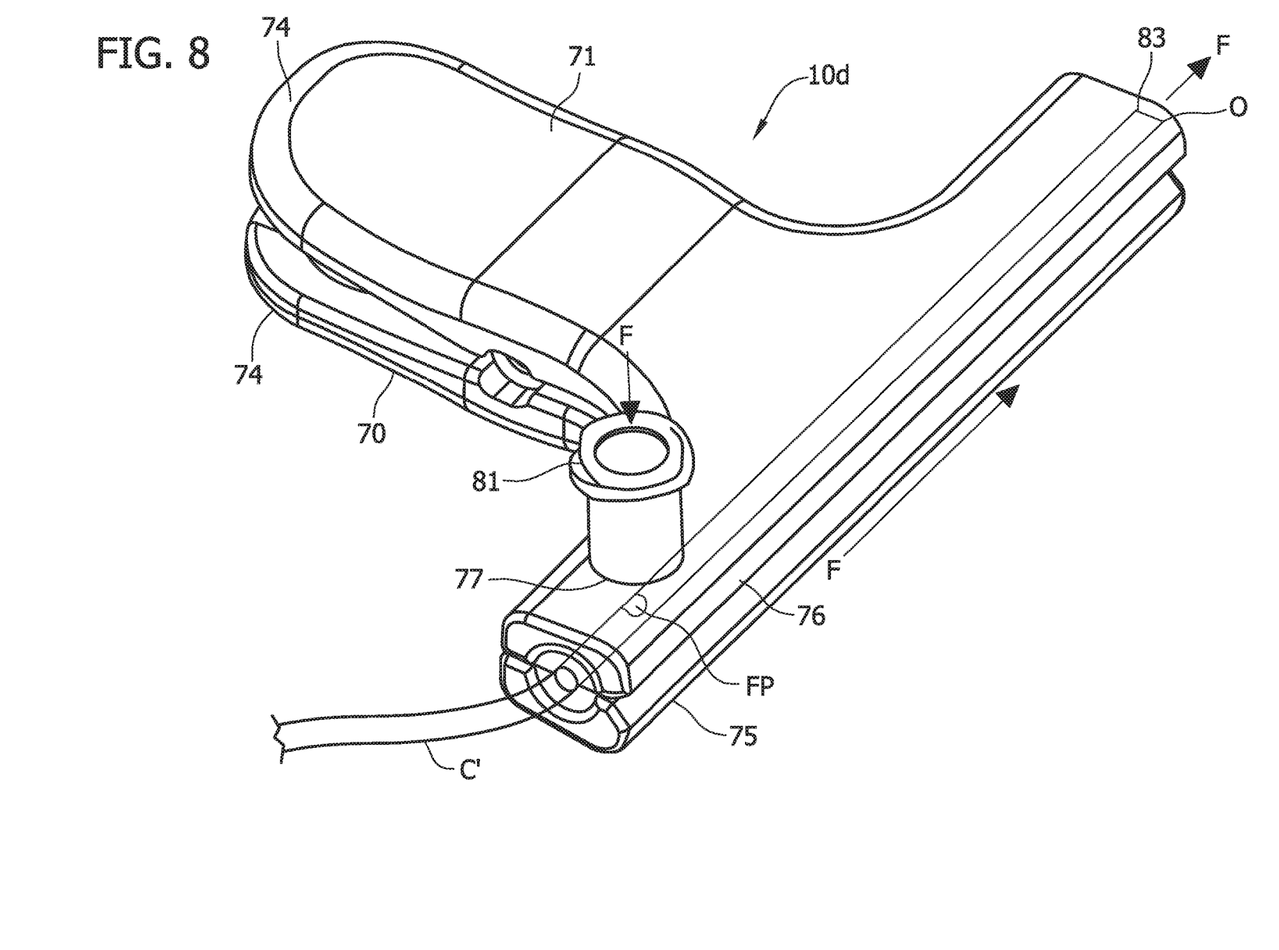
FIG. 8 is similar to FIG. 4, except the medical instrument is shown received in the cleaning device during a cleaning process.

FIG. 8 illustrates a method of using cleaning device 10d with a catheter C' having a distal opening and a flush port proximal of the distal opening. Such a catheter might include catheters having a cutting element which extends through a distal end of the catheter body and a material collection chamber located between the flush port and the distal end of the catheter. Catheter C' is inserted into cleaning device 10d by compressing, pinching or squeezing handle portion 74 of upper half 71 and handle portion 74 of lower half 70 separating luminal portion 75 of upper half 71 from luminal portion 75 of lower half 70. A distal end of catheter C' is inserted into the flushing chamber or lumen 76 and positioned where distal opening O is located adjacent, proximal or extending through outlet 83 and the flush port FP is located within inlet cavity 77.

Once catheter C' has been inserted flush port FP may be adjacently aligned with inlet port 81, although it should be understood that alignment of the openings and the ports are not required so long as fluid entering through the inlet port is caused to flow into the catheter through the flush port and out of the catheter through the distal opening O, as described below. The compression, pinching or squeezing of handle portions 74 of the upper half 71 and lower half 70 is halted and luminal portions 75 of the upper half 71 and lower half 70 enclose the distal tip of catheter C within flushing chamber or lumen 76 of cleaning device 10d. As the luminal portions 74 enclose the distal tip of catheter C', the elastic material of flush chamber or lumen 76 seals around the outer diameter of the catheter and assists in directing fluid flow through the lumen of catheter C'. Seal 79 forms a seal about a proximal portion of the flushing chamber or lumen 76. Fluid F is then inserted into inlet port 81 and caused to flow from the inlet port into the flush port FP of the catheter, through an interior space in the catheter body and then out of the catheter body through the distal opening O and out of the flushing chamber through outlet 83.

The above description and the drawings are provided for the purpose of describing embodiments of the invention and are not intended to limit the scope of the invention in any way. It will be apparent to those skilled in the art that various modifications and variations can be made without departing from the spirit or scope of the invention. Thus, it is intended that the present invention cover the modifications and variations of this invention provided they come within the scope of the appended claims and their equivalents. Further, while choices for materials and configurations may have been described above with respect to certain embodiments, one of ordinary skill in the art will understand that the materials and configurations described are applicable across the embodiments.

What is claimed is:

1. A cleaning device for cleaning a medical instrument, the medical instrument having a distal end portion defining an instrument lumen and proximal and distal openings in fluid communication with the instrument lumen, the cleaning device comprising:
 a flushing chamber having opposite proximal and distal ends, and a length extending between the proximal and distal ends, wherein the flushing chamber comprises an upper luminal portion and a lower luminal portion;
an inlet port in fluid communication with the flushing chamber and configured for fluid connection to a source of fluid; and
an outlet port in fluid communication with the flushing chamber such that fluid directed into the flushing chamber through the inlet port can be discharged from the flushing chamber through the outlet port,
wherein the flushing chamber is selectively openable along its length to an open position, in which the upper and lower luminal portions are separated from one another so that the distal end portion of the medical instrument is insertable into the flushing chamber, and selectively closable along its length to a closed position, in which the upper and lower luminal portions enclose and fluidly seal around the distal end portion of the medical instrument,
wherein each of the upper and lower luminal portions is elastic,
wherein each of the upper and lower luminal portions comprises a proximal section proximal of the inlet port along the length of the flushing chamber, a distal section distal of the outlet port along the length of the flushing chamber, and a central section between the inlet port and the outlet port along the length of the flushing chamber, and
wherein when the flushing chamber is in the closed position, the proximal sections of the upper and lower luminal portions are configured to form a proximal fluid seal about the medical instrument proximal of the proximal opening, the distal sections of the upper and lower luminal portions are configured to form a distal fluid seal distal of the distal opening, and the central sections of the upper and lower luminal portions are configured to form a central fluid seal about the distal end portion of the medical instrument between the proximal and distal openings.

2. The cleaning device of claim 1, further comprising an upper handle portion and a lower handle portion that are coupled to one another by a hinge, the upper luminal portion being secured to the upper handle portion and the lower luminal portion being secured to the lower handle portion, wherein the lower handle portion and the upper handle portion are pivotable relative to one another about the hinge for opening and closing the flushing chamber.

3. The cleaning device of claim 2, further comprising a spring secured to the upper and lower handle portions and biasing the flushing chamber in the closed position.

4. The cleaning device of claim 2, wherein the handle portions extend in a direction generally transverse to the length of the flushing chamber.

5. The cleaning device of claim 4, wherein the handle portions are movable in a direction toward one another to open the flushing chamber, and in a direction away from one another to close the flushing chamber.

6. The cleaning device of claim 1, wherein the upper and lower luminal portions are coupled to one another by a hinge.

7. The cleaning device of claim 6, further comprising a spring biasing the flushing chamber in the closed position.

8. The cleaning device of claim 1, wherein the inlet port is connected to the flushing chamber such that the proximal opening in the distal end portion of the medical instrument is adjacent the inlet port when the distal end portion is enclosed and fluidly sealed in the flushing chamber.

9. The cleaning device of claim 1, wherein the outlet port is connected to the flushing chamber such that the distal opening in the distal end portion of the medical instrument is adjacent the outlet port when the distal end portion is enclosed and fluidly sealed in the flushing chamber.

10. The cleaning device of claim 9, wherein the flushing chamber includes a stop at the distal end of the flushing chamber.

11. The cleaning device of claim 1, wherein the distal end of the flushing chamber is open.

12. A combination comprising the cleaning device of claim 1 a medical instrument having a distal end portion defining an instrument lumen and proximal and distal openings in fluid communication with the instrument lumen.

13. A method of cleaning a medical instrument having a distal end portion defining an instrument lumen, and proximal and distal openings in fluid communication with the instrument lumen, the method comprising:
providing a cleaning device including
a flushing chamber having opposite proximal and distal ends, and a length extending between the proximal and distal ends, wherein the flushing chamber comprises an upper luminal portion and a lower luminal portion; and
an inlet port in fluid communication with the flushing chamber and configured for fluid connection to a source of fluid; and
an outlet port in fluid communication with the flushing chamber such that fluid directed into the flushing chamber through the inlet port can be discharged from the flushing chamber through the outlet port,
wherein the flushing chamber is selectively openable along its length to an open position, in which the upper and lower luminal portions are separated from one another so that the distal end portion of the medical instrument is insertable into the flushing chamber, and selectively closable along its length to a closed position, in which the upper and lower luminal portions enclose and fluidly seal around the distal end portion of the medical instrument,
wherein each of the upper and lower luminal portions is elastic,
wherein each of the upper and lower luminal portions comprises a proximal section proximal of the inlet port along the length of the flushing chamber, a distal section distal of the outlet port along the length of the flushing chamber, and a central section between the inlet port and the outlet port along the length of the flushing chamber, and
wherein when the flushing chamber is in the closed position, the proximal sections of the upper and lower luminal portions are configured to form a proximal fluid seal about the medical instrument proximal of the proximal opening, the distal sections of the upper and lower luminal portions are configured to form a distal fluid seal distal of the distal opening, and the central sections of the upper and lower luminal portions are configured to form a central fluid seal about the distal end portion of the medical instrument between the proximal and distal openings;
opening the flushing chamber;
inserting the distal end portion of the medical instrument into the opened flushing chamber;
closing the flushing chamber after said inserting the distal end portion, wherein the distal end portion of the medical instrument is enclosed and fluidly sealed within the flushing chamber; and introducing fluid into the inlet port of the flushing chamber, after said closing the flushing chamber, to create a pressurized flow of fluid through the proximal port of the flushing chamber, into the proximal opening in the medical instrument, through the instrument lumen of the medical instrument, and out the distal opening in the medical instrument, wherein residual matter from previous usage of the medical instrument is ejected with the fluid flow out through the distal opening in the medical instrument.

14. The method of claim 13, wherein said opening the flushing chamber comprises pivoting upper and lower luminal portions of the flushing chamber away from one another about a hinge.

15. The method of claim 14, wherein said opening the flushing chamber further comprises squeezing together handle portions operatively connected to respective upper and lower luminal portions of the flushing chamber to impart pivoting of the upper and lower luminal portions about the hinge.

16. The method of claim 13, further comprising directing the fluid with the residual matter ejected from the distal opening of the medical instrument into the outlet port of the cleaning device.

* * * * *